(12) United States Patent
Gagnon

(10) Patent No.: US 8,440,976 B2
(45) Date of Patent: May 14, 2013

(54) METHOD FOR OPTIMIZING STEP SIZE IN A MULTI-STEP WHOLE-BODY PET IMAGING

(75) Inventor: Daniel Gagnon, Twinsburg, OH (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 206 days.

(21) Appl. No.: 13/010,237

(22) Filed: Jan. 20, 2011

(65) Prior Publication Data

US 2012/0187300 A1    Jul. 26, 2012

(51) Int. Cl.
*G01T 1/166* (2006.01)
(52) U.S. Cl.
USPC .................... 250/363.09; 250/363.07
(58) Field of Classification Search ............... 250/252.1, 250/363.03, 363.04, 363.07, 363.09
See application file for complete search history.

(56) References Cited

U.S. PATENT DOCUMENTS 5,224,135 A    6/1993    Toki

FOREIGN PATENT DOCUMENTS

| JP | 03-251784 | 11/1991 |
| JP | 04-170941 | 6/1992 |
| JP | 05-130984 | 5/1993 |
| JP | 08-313636 | 11/1996 |
| JP | 2001-194459 | 7/2001 |

OTHER PUBLICATIONS

Japan Industries Association of Radiological Systems, "Medical Image/Radiological Equipment Hand Book", Nago Bijutsu Insatsu Kabushiki Kaisha, 2001, p. 190-191(with Partial English-language translation).
International Search Report issued Apr. 24, 2012, in PCT/JP2012/051243 (with English-language translation).

*Primary Examiner* — Mark R Gaworecki
(74) *Attorney, Agent, or Firm* — Oblon, Spivak, McClelland, Maier & Neustadt, L.L.P.

(57) ABSTRACT

A method of imaging a region of interest (ROI) in an object, the ROI having an axial extent greater than an axial FOV of a PET scanner. The method includes determining a number of overlapping scans of the PET scanner necessary to image at least the axial extent of the ROI, wherein each scan has a same axial length equal to the axial FOV, and each scan overlaps an adjacent scan by a predetermined overlap percentage of the axial length of each scan. The method includes determining a total amount of excess scanning length of the scans based on the number, the axial extent of the ROI, and the axial FOV, and determining a new overlap percentage so that a new total amount of excess scanning length is zero.

14 Claims, 12 Drawing Sheets

TYPICAL WHOLE-BODY
~ 200 M counts

TYPICAL WHOLE-BODY
~ 200 M counts determine a minimum number of successive overlapping scans (n) of
the PET scanner necessary to image at least the axial extent of the
object (L), wherein each scan of the successive scans has a same axial
length (S) equal to the axial field of view of the PET scanner, and each
scan overlaps an adjacent scan by a predetermined minimum overlap
percentage ($\alpha_{min}$) of the axial length of each scan, i.e.,
$$n = \text{round}\{(L - \alpha_{min} S) / (S - \alpha_{min} S)\}$$
— 921 determine a total amount of excess scanning length (E) of the
successive scans based on the minimum number of successive scans
determined in the determining step, the axial extent of the object, and
the axial field of view, i.e.,
$$E = S + (n-1)(1 - \alpha_{min})S - L$$
— 922 determine a new overlap percentage ($\alpha'$) based on the determined total
amount of excess scanning length and the predetermined minimum
overlap percentage, so that a new total amount of excess scanning
length, as determined with the new overlap percentage, is zero, i.e.,
$$\alpha' = \alpha_{min} + E/(n-1)S$$
— 923

FIG. 9C

METHOD FOR OPTIMIZING STEP SIZE IN A MULTI-STEP WHOLE-BODY PET IMAGING

FIELD

Embodiments described herein relate generally to methods of imaging an object using radiation detectors, such as for gamma cameras and positron emission tomography (PET) scanners.

BACKGROUND

The use of gamma ray detectors in general, and positron emission tomography or PET detectors in particular, is growing in the field of medical imaging. In PET imaging, a radiopharmaceutical agent is introduced into an object to be imaged via injection, inhalation, or ingestion. After administration of the radiopharmaceutical, the physical and bio-molecular properties of the agent will cause it to concentrate at specific locations in the human body. The actual spatial distribution of the agent, the intensity of the region of accumulation of the agent, and the kinetics of the process from administration to its eventual elimination are all factors that may have clinical significance. During this process, a positron emitter attached to the radiopharmaceutical agent will emit positrons according to the physical properties of the isotope, such as half-life, branching ratio, etc.

The radionuclide emits positrons, and when an emitted positron collides with an electron, an annihilation event occurs, wherein the positron and electron are destroyed. Most of the time, an annihilation event produces two gamma rays (at 511 keV) traveling at substantially 180 degrees apart.

By detecting the two gamma rays, and drawing a line between their locations, i.e., the line-of-response (LOR), one can retrieve the likely location of the original disintegration. While this process will only identify a line of possible interaction, by accumulating a large number of those lines, and through a tomographic reconstruction process, the original distribution can be estimated. In addition to the location of the two scintillation events, if accurate timing (within few hundred picoseconds) is available, a time-of-flight (TOF) calculation can add more information regarding the likely position of the event along the line. Limitations in the timing resolution of the scanner will determine the accuracy of the positioning along this line. Limitations in the determination of the location of the original scintillation events will determine the ultimate spatial resolution of the scanner, while the specific characteristics of the isotope (e.g., energy of the positron) will also contribute (via positron range and co-linearity of the two gamma rays) to the determination of the spatial resolution the specific agent.

The above described detection process must be repeated for a large number of annihilation events. While each imaging case must be analyzed to determine how many counts (i.e., paired events) are required to support the imaging task, current practice dictates that a typical 100-cm long, $^{18}$FDG (fluoro-deoxyglucose) study will need to accumulate several hundred million counts. The time required to accumulate this number of counts is determined by the injected dose of the agent and the sensitivity and counting capacity of the scanner.

The scanner will acquire counts in a three-dimensional mode, meaning that each line emitted from the object and crossing two detector elements is potentially detected. Thus, for example, the two emission points A and B disposed as indicated in FIG. 1 have a different probability of being detected. The point B in the middle of the center of the axial line has the maximum chance of being detected as it has the largest solid angle, including the two legs of the annihilation event. Point A supports a smaller angle, while a point right at the edge of the axial FOV would have a minimal chance of being detected. This analysis is used to determine the overall scanner sensitivity, which has a triangular shape typical of a completely open 3D scanner, as shown on the right-hand side of FIG. 1.

A special case of this situation is when, by electronics design or otherwise, the largest angles are cut off from the analysis since large oblique angles of incidence may present some challenges for some reconstruction algorithms. In this case, the typical triangle would be flattened at some point related to the cut-off angle.

This triangular axial sensitivity profile is useful as the typical 100 cm PET studies require more than one axial FOV of the scanner. Several bed positions need to be added. Usually, 50% overlap between steps is optimal as it creates a flat sensitivity over the central portion of the image, as show in FIG. 2, which shows the scanner FOV with respect to the total length requested by the user.

A repeat of the same FOV with a 50% overlap per scan is illustrated in FIG. 3.

A fixed step size will likely create an undershoot or an overshoot of the targeted length. Since under-sampling the region of interest is not an option, the scanner is likely to take an extra step to cover the entire area. In this case, the overshoot area, shown at the bottom of FIG. 3, is small. In practice, the imaging system may only present achievable length by forcing the user to step through the possible discrete length. Either way, the total length of the PET image will slightly overshoot the length the clinician would have selected.

This effect will be exacerbated in larger axial FOV scanners, as shown in FIG. 4, in which the overshoot area is visibly more important. This effect is also proportionally increased when the requested area of interest is shorter, as shown in FIG. 5.

An alternative approach is to design the system with a continuous bed motion in which the speed profile and the total length scanned can be controlled more precisely. However, continuous bed motion is not always available is all systems and definitely adds complexity to data acquisition and reconstruction.

Thus, as illustrated in FIG. 3-5, in a step-and-shoot system, a significant amount of time and counts can be spent outside of the area of interest, meaning that the same imaging resources could have been spent more efficiently.

Conventional PET scanners have an axial FOV between 16 and 22 cm to cover a typical 100 cm length. With an overlap of 50%, 8 to 12 steps are typically required, with possibly 8-12% of imaging resources being spent outside the area of interest. Other studies, like lung or head-neck imaging, are generally 30 to 50 cm long, where the waste of imaging resources can be as high as 20-30%.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 9A-9C are flowcharts illustrating the steps in three embodiments disclosed herein.

DETAILED DESCRIPTION

Figure 1:
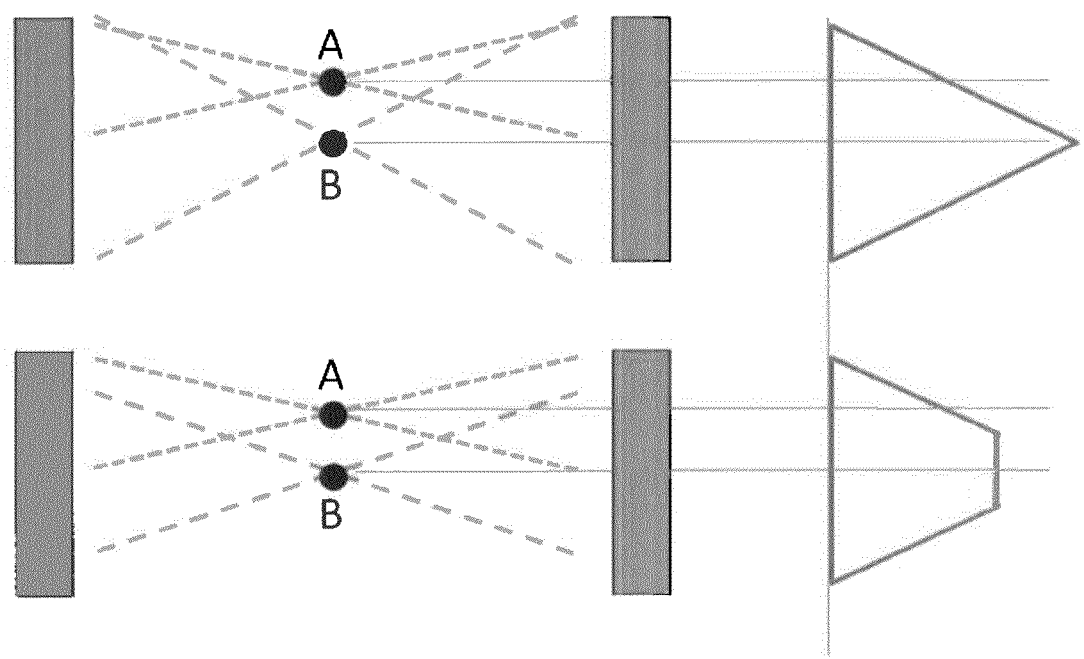
FIG. 1 illustrates sensitivity of a PET scanner for different events.
Figure 2:
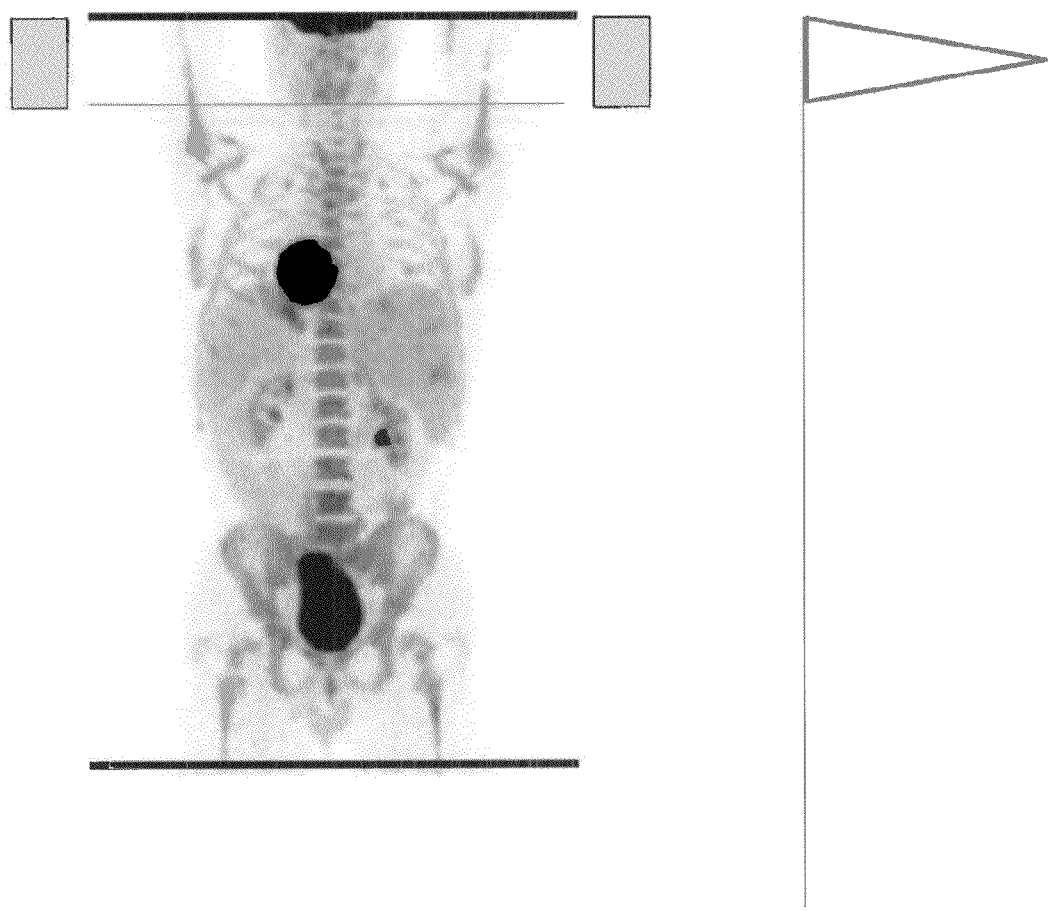
FIG. 2 illustrates an axial sensitivity profile for a typical PET scanner over one axial field of view.
Figure 3:
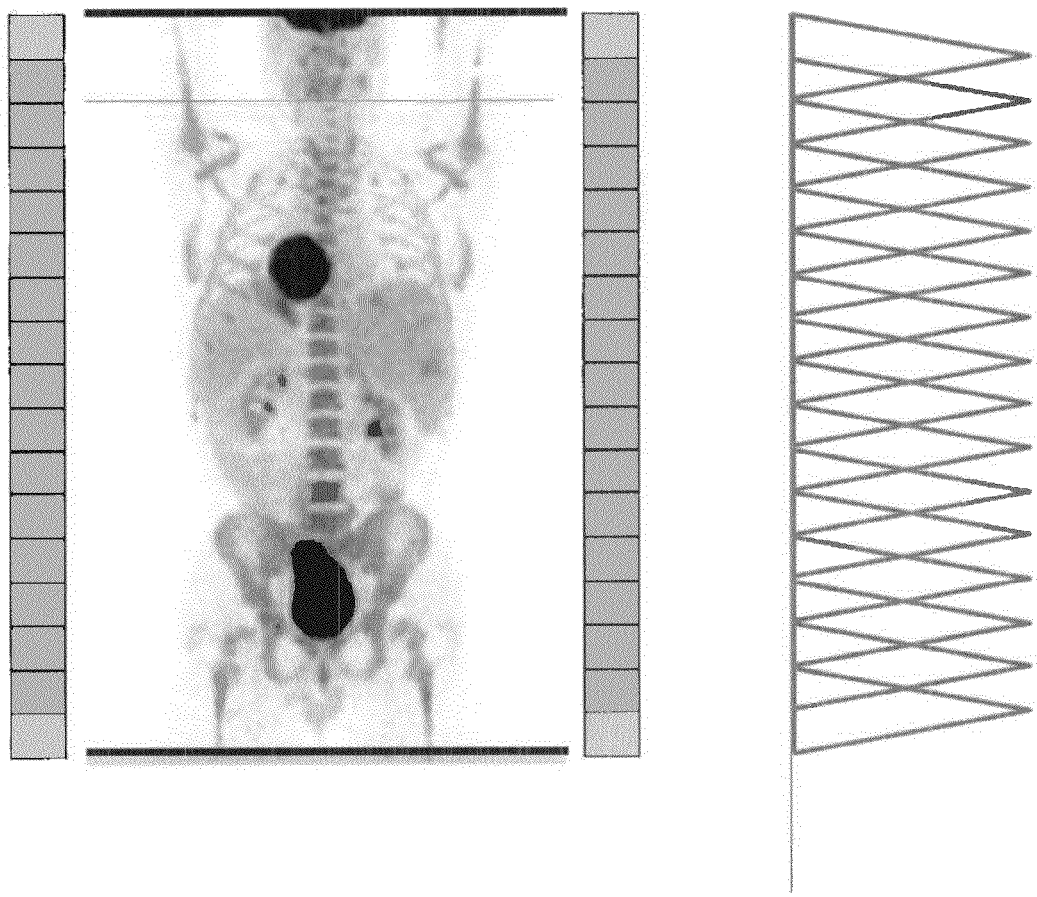
FIG. 3 illustrates the axial sensitivity profiles for a multi-step PET scan having 50% overlap for each scanning step.
Figure 4:
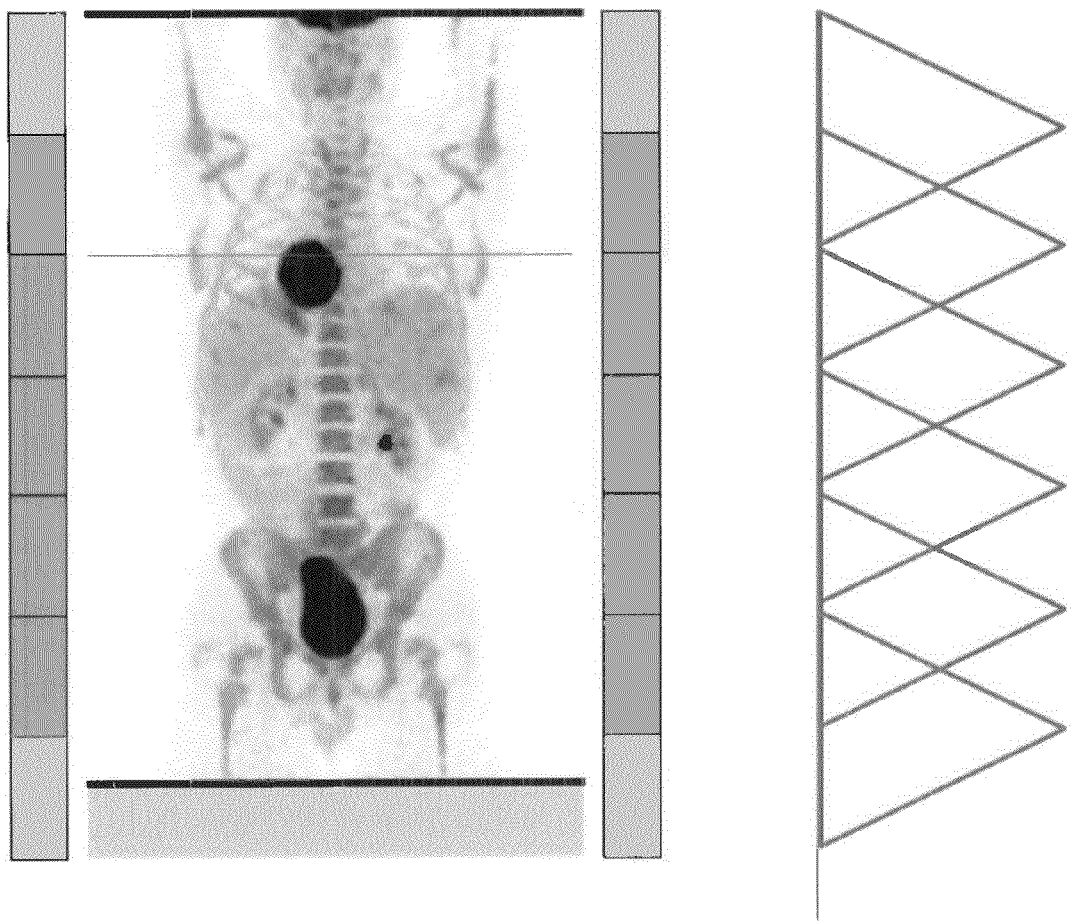
FIGS. 4 and 5 illustrate overshoot of the targeted length to be scanned using a fixed step-size scan.

Embodiments described herein relate to a new method of optimizing the step-size in multi-step PET imaging using an PET scanner.

In one embodiment, a method of imaging a region of interest in an object, the region of interest having an axial extent greater than an axial field of view of a PET scanner includes: (1) determining a minimum number of successive overlapping scans of the PET scanner necessary to image at least the axial extent of the region of interest, wherein each scan of the successive scans has a same axial length equal to the axial field of view of the PET scanner, and each scan overlaps an adjacent scan by a fixed percentage of the axial length of each scan; (2) determining a total amount of excess scanning length of the successive scans based on the minimum number of successive scans determined in the determining step, the axial extent of the region of interest, and the axial field of view; and (3) determining an initial starting point of a first scan of the successive scans so that the total excess scanning length is equally allocated on each end of the object in an axial direction.

In another embodiment, a method of imaging a region of interest in an object, the region of interest having an axial extent greater than an axial field of view of a PET scanner includes: (1) determining a combination of (a) a number of successive overlapping scans of the PET scanner necessary to image the axial extent of the region of interest, wherein each scan of the successive scans has a same axial length equal to the axial field of view of the PET scanner, and (b) an overlap percentage of the axial length of each scan by which each scan overlaps an adjacent scan, so that a total length of the determined number of successive scans exactly equals the axial extent of the region of interest; and (2) setting a scan time for each of the successive scans based on the determined number and the determined overlap percentage.

In another embodiment, a method of imaging a region of interest in an object, the region of interest having an axial extent greater than an axial field of view of a PET scanner, includes: (1) determining a minimum number of successive overlapping scans of the PET scanner necessary to image at least the axial extent of the region of interest, wherein each scan of the successive scans has a same axial length equal to the axial field of view of the PET scanner, and each scan overlaps an adjacent scan by a predetermined minimum overlap percentage of the axial length of each scan; (2) determining a total amount of excess scanning length of the successive scans based on the minimum number of successive scans determined in the determining step, the axial extent of the region of interest, and the axial field of view; and (3) determining a new overlap percentage based on the determined total amount of excess scanning length and the predetermined minimum overlap percentage, so that a new total amount of excess scanning length, as determined with the new overlap percentage, is zero.

Figure 5:
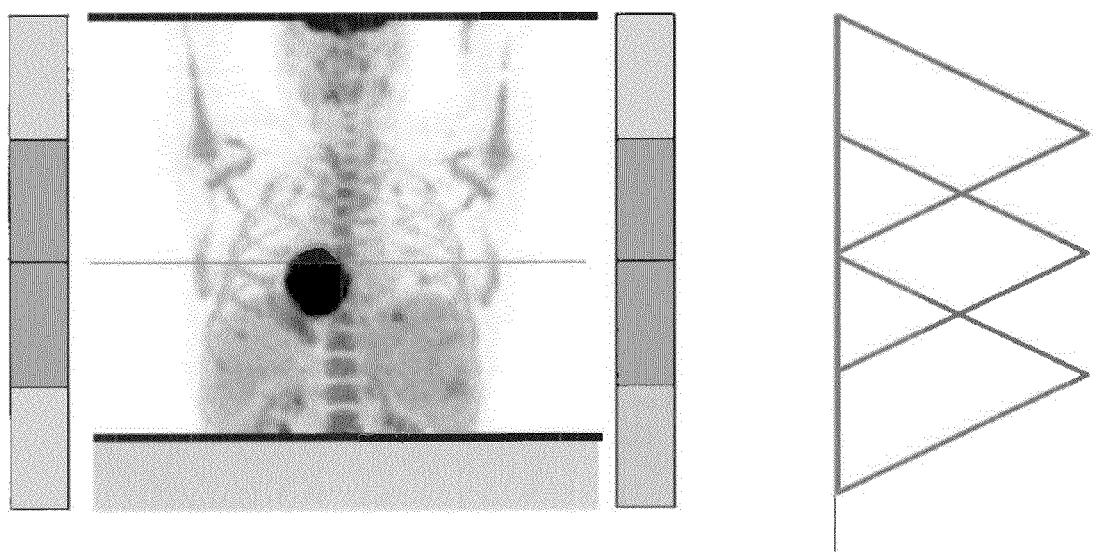
Figure 6:
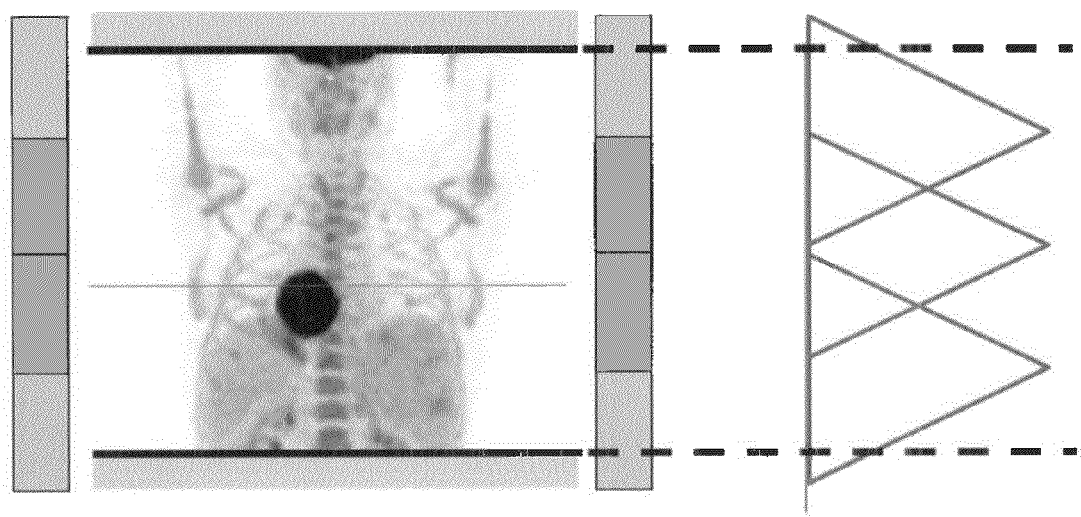
FIG. 6 illustrates a scanning method according to a first embodiment.

In one embodiment, no attempt is done to minimize the number of steps or the overlap, but the imaging resources are optimized on the area of interest. For example, as shown in FIG. 6, using the same example in FIG. 5, the axial extent of the first scan is shifted from that shown in FIG. 5 so that the lower sensitivity corresponds to a region outside the region of interest.

In this embodiment, the wasted areas at the beginning and end of the scan sum to the same area as before, but there is lesser sensitivity in those areas. Thus, once the overall scan length is established and the number of steps calculated to at least cover the entire area (and quite possibly more), the scanner splits the difference between the overall axial extent of the scan and the extent of the region of interest, at the beginning and end of the scan.

Figure 9A:
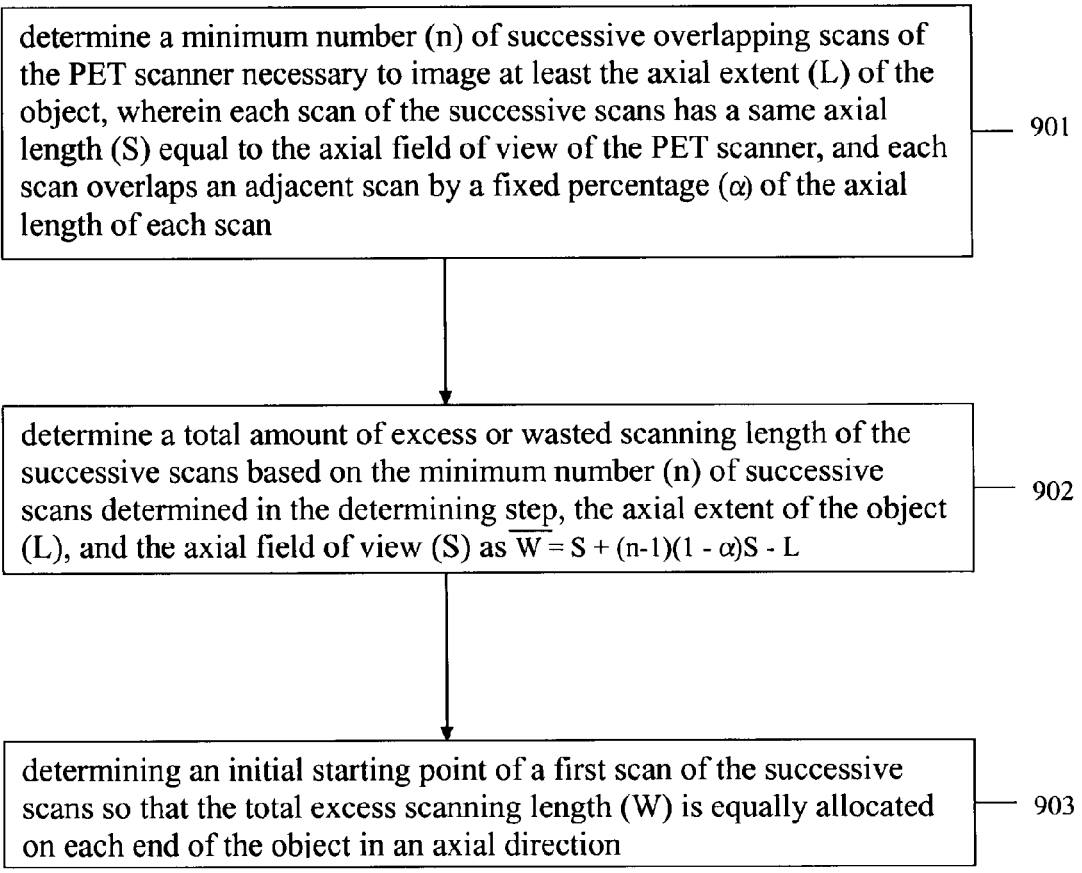

FIG. 9A illustrates the steps in a method of scanning according to this embodiment. In particular, assuming a fixed overlap in each step of $\alpha S$ ($\alpha<1$), where S is the length of the scanner axial FOV and $\alpha$ is predetermined based on desired sensitivity (see below), the number of scan steps n is elected in step 901 so that the distance scanned D is greater than L, the axial extent of the region of interest to be scanned, i.e., so that:

$$D=S+(n-1)(1-\alpha)S>L.$$

Further, in step 902, the wasted area (undershoot plus overshoot) is determined by the formula by $W=D-L$. In step 903, the starting point of the scan is selected so that the undershoot equals $W/2$ and the overshoot equals $W/2$.

Figure 7:
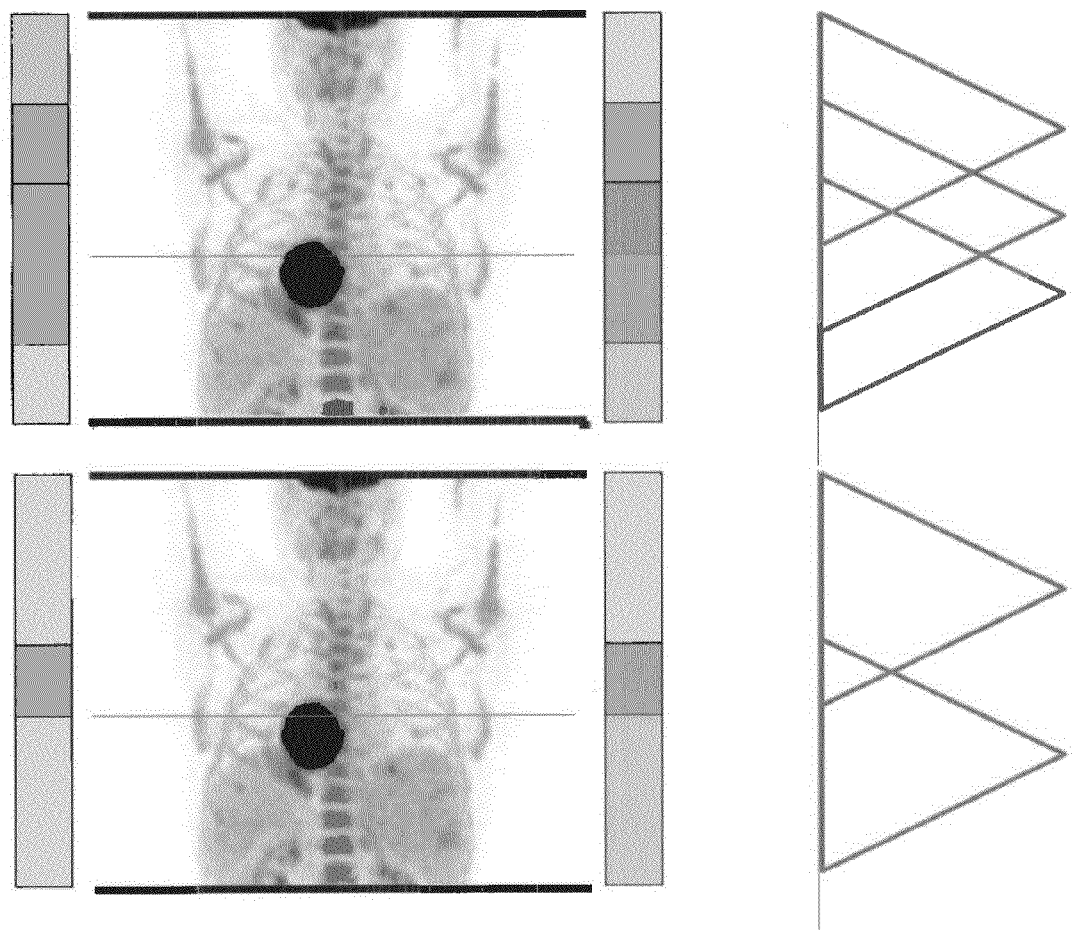
FIG. 7 illustrates a scanning method according to a second embodiment is which undershoot and overshoot are eliminated by adjusting the overlap percentage.

In a second embodiment, the step size is adjusted to match the actual length of imaging. In addition, imaging time is adjusted to compensate for the change in the step size so that fewer, large steps would each be imaged for a relatively longer period of time, while more, smaller steps would each be imaged for a relatively shorter period of time. FIG. 7 illustrates an example of the shrinking of the step size (top example) and an example of the stretching of the step size (bottom example) and the corresponding sensitivity profile. As is clear from FIG. 7, the adjustment of the step size will cause the overall axial sensitivity to no longer be flat.

Suppose that the axial length is exactly two steps with a 50% overlap. As we increase the area to be covered, the amount of overlap is reduced to match the increased distance. As the length of the scan increases, and based on either a threshold on axial sensitivity or on an arbitrary criterion set by the user, the overlap will be too small at some point, and a third scanning step is introduced with possible more that 50% overlap to match the distance, and so on.

Figure 9B:
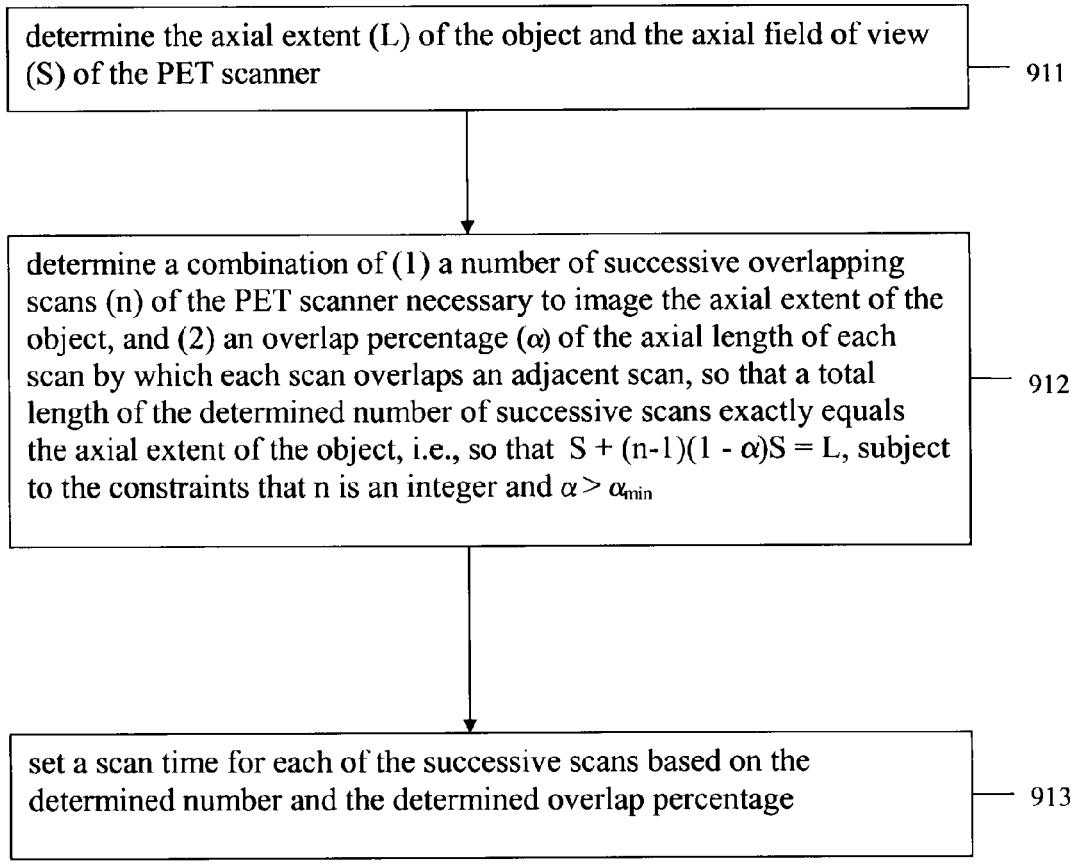

FIG. 9B illustrates the steps in a method of imaging according to the second embodiment. In step 911, the axial extent to be scanned (L) and the axial FOV (S) are determined.

In step 912, the combination of the overlap in each step ($\alpha$) and the number of scan steps n are determined so that the distance scanned D is exactly equal to L, i.e., so that:

$$D=S+(n-1)(1-\alpha)S=L.$$

In this embodiment, $\alpha$ is constrained to be greater than a predetermined minimum value, and n is constrained to be an integer. In general, multiple solutions in $n-\alpha$ space will exist.

In this embodiment, the wasted area (undershoot plus overshoot), which is given by $W=D-L$, equals zero. Thus, in this embodiment, the starting point of the scan is selected as the beginning of the region of interest to be scanned.

In step 913, the scan time for each of the n scans is set based on the determined number of scans and the determined overlap percentage α. Typically, a PET acquisition is defined to accumulate a certain total number of counts or a certain count density over the region of interest. The imaging time for a single step of a multiple step PET acquisition is selected to support this requirement. If a new step size and/or a new overlap percentage is used, the overall efficiency of the utilization of imaging resources can be used to adjust the imaging time per step. For example, in reference to the two scenarios shown in FIG. 7, if the nominal desired count density can be achieved with a scanning time of one minute per step, the top scenario covering the exact desired length, would required three steps of with scanning times of fifty seconds each due to a larger overlap, while the bottom scenario would require two steps with scanning times of 75 seconds each due to the smaller overlap. In general, the smaller the overlap, the larger the scanning time per step.

In a third embodiment, the step sizes and scanning method is a combination of the first and second embodiments set forth above. An algorithm is used to calculate the amount of overlap between steps and the amount of undershoot and overshoot along the axis of the image. First, for the nominal case, there is a fixed overlap in each step of αS (α<1) and a waste region of βS (β<1) at each end, both expressed as a fraction of the scanner axial FOV S. If L is the axial extent of the region of interest, which is to be scanned in n steps, the following relation holds:

$$L+2\beta S=S+(n-1)(1-\alpha)S \qquad (1)$$

If L and S are given, n can be calculated along with α and β, subject to appropriate constraints. For example, with the constraints that β can only decrease for a fixed initial value and 0.4<α<0.6, this problem can be solved using a variety of optimization algorithms.

FIG. 9C illustrates steps in the method of scanning according to the third embodiment.

Without a waste region (β=0) and a minimum allowable value for α (i.e., $\alpha_{min}$), the optimization to find n and α is straightforward, as set forth in the following steps.

If $\alpha=\alpha_{min}$ is the minimum allowable overlap fraction, then the number of steps is derived in step 921 from Equation 1, resulting in the equation:

$$n=\text{round}\{(L-\alpha_{min}S)/(S-\alpha_{min}S)\}, \qquad (2)$$

with the division rounded up to the next integer using the round { } function.

In step 922, the extra length E from performing n steps with the minimum overlap is calculated as:

$$E(\alpha_{min})=S+(n-1)(1-\alpha_{min})S-L, \qquad (3)$$

which is again based on Equation 1.

In step 923, letting $\alpha'=\alpha_{min}+\Delta\alpha$ and setting E(α')=0 in Equation 3 and solving for Δα results in an optimal overlap α' for which there is no extra space:

$$\alpha'=\alpha_{min}+E(\alpha_{min})/(n-1)S \qquad (4)$$

For example, for a 55 cm region of interest using a scanner having a 20 cm axial FOV with a minimum of 50% overlap, the number of steps according to Equation 2 is:

$$n=\text{round}\{(55-(0.5)(20))/(20-(0.5)(20))\}=5,$$

but the extra distance E cover by n=5 steps, according to Equation 3, is:

$$E=20+(5-1)(1-0.5)(20)-55=5 \text{ cm}.$$

The new overlap to produce exactly a 55 cm scan is, according to Equation 4:

$$\alpha'=0.5+5/(5-1)(20)=0.5625 \text{ or } 56.25\%.$$

Thus, approximately 9% of the imaging resources (5/55) are used to directly support the requested region of interest that can either be used to improve the image quality—9% more counts over the region of interest—or reduce imaging time per step by 9% to the preference of the user.

The same problem with a 32 cm scanner would result in n=3, E=9 cm, α'=64% and an overall better resource utilization of 16%.

Similarly, additional constraints can be set to also consider the beginning and end "wasted" areas. In practice, the user is presented with overall imaging preferences, such as acceptable variation in axial uniformity and a minimum slice sensitivity. In some cases, depending on the set preferences, multiple combinations of steps and overlap percentage could exist.

Figure 8:
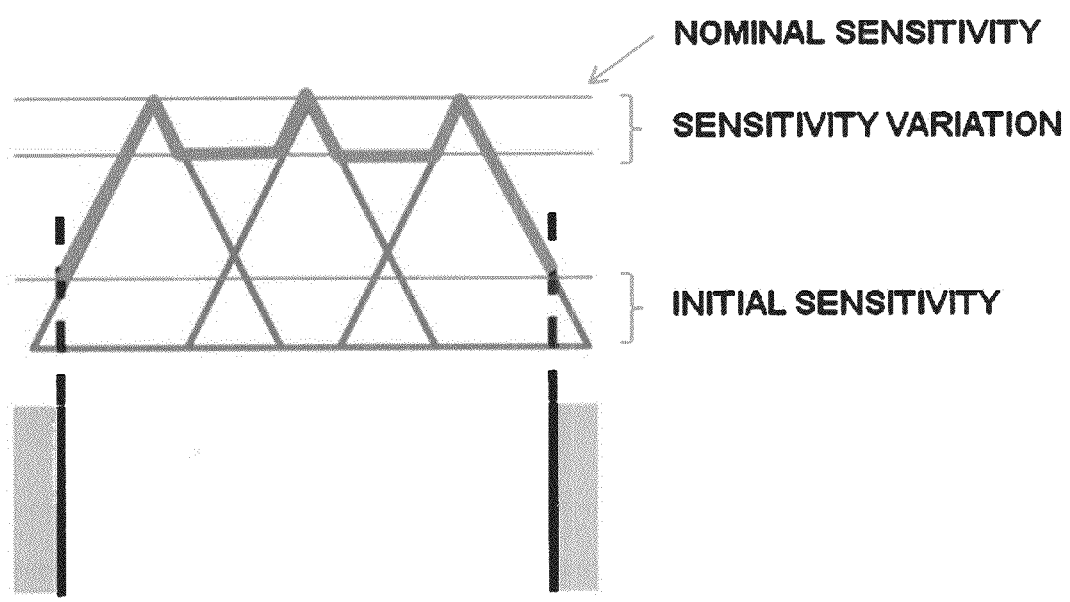
FIG. 8 illustrates initial and nominal sensitivity profiles.

In reference to FIG. 8, an overall sensitivity profile is shown (bold line). Any given point of the profile is composed from the summation of all contributions from all scanning steps. In full 3D acquisition mode, a ring of length S will produce a triangular sensitivity profile with a peak at S/2. Depending on the overlap α, the overall sensitivity at any given scanning position will be the sum of one or more of the triangular sensitivity profiles, i.e., C(x)=T(x)+T(x−S+αS)+ . . . , where T(x) is a first triangle, T(x−S+αS) is a second (shifted) triangle overlapping the first triangle by αS, etc.

As described above, the feature that is targeted in the imaging protocol is the total number of counts (or count density). Accordingly, the clinical user would specify the minimum initial sensitivity (at the beginning and end of the scan) and the maximum (nominal) variation (in the central part of the scan). While the user is interested more in the vertical axis of sensitivity, the system needs to convert the user's sensitivity requirements into movement along the horizontal axis. Clearly, the minimum initial sensitivity is directly proportional to the β introduced earlier, i.e., β=0.5*(initial sensitivity/nominal sensitivity). Similarly, the overlap α directly affects the nominal sensitivity. In the second embodiment described above, the overlap percentage α can be determined by determining the overlap percentage α that results in the function C(x) having a maximum value equal to the nominal sensitivity set by the user.

In the previous example of L=55 cm and a scanner FOV of S=32 cm, one result is n=3 steps and α'=64% overlap. However, other solutions are n=2 steps and α'=22% overlap and n=4 steps with α'=76% overlap. Usually, the smaller number of steps is preferable, and a constraint on uniformity will establish the best option. For example, having only α'=22% overlap would typically result in an unacceptable reduction in sensitivity in the middle of the scanner. Depending of the overall allowable parameters, more complex optimization algorithms can be used.

The method set forth above will optimize the use of expensive imaging resources and provide the best possible information on the selected region of interest. The conventional technology of fixed step-and-shoot will be at more and more of a disadvantage as larger axial FOV scanners are produced, and as more and more applications require fewer steps.

Thus, embodiments described herein will provide an optimal utilization of valuable imaging resources by minimizing the amount of waste outside of the requested imaging range, while taking into account image quality and scanner sensitivity limits.

Figure 10:
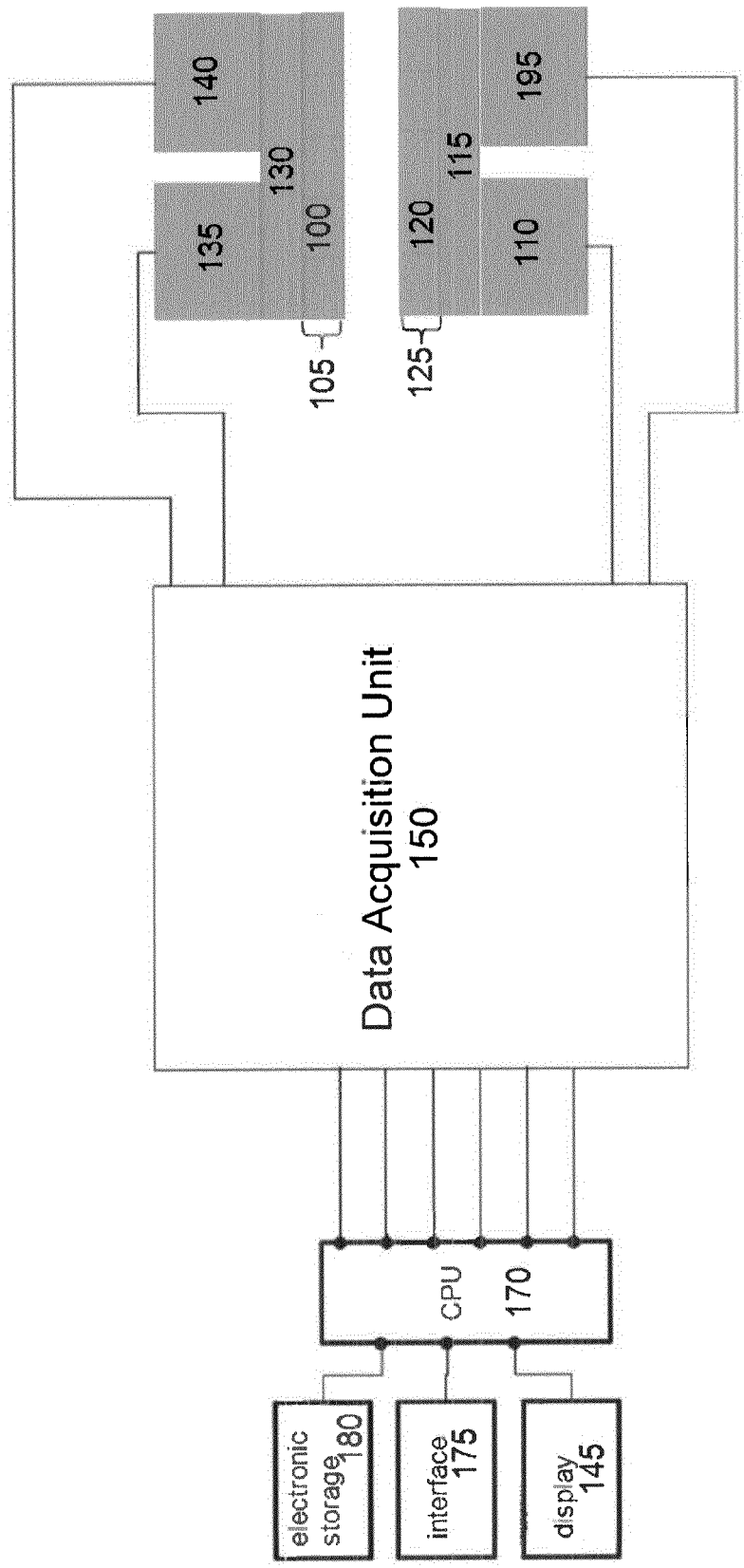
FIG. 10 illustrates a PET data acquisition and processing system.

FIG. 10 is a schematic drawing of a gamma ray detection system that can be used to obtain gamma ray or PET event information according to embodiments of the present advancements. In FIG. 10, photomultiplier tubes 135 and 140 are arranged over light guide 130, and the array of scintillation crystals 105 is arranged beneath the light guide 130. A second array of scintillation crystals 125 is disposed opposite the scintillation crystals 105 with light guide 115 and photomultiplier tubes 195 and 110 arranged thereover. The photomultiplier tubes, light guide, and scintillation crystals can form a detector module, wherein the gamma ray detection system includes a plurality of detector modules arranged in a ring.

In FIG. 10, when gamma rays are emitted from a body under test (not shown), the gamma rays travel in opposite directions, approximately 180° from each other. Gamma ray detection occurs simultaneously at scintillation crystals 100 and 120, and a scintillation event is determined when the gamma rays are detected at scintillation crystals 100 and 120 within a predefined time limit. Thus, the gamma ray timing detection system detects gamma rays simultaneously at scintillation crystals 100 and 120. However, for simplicity only, gamma ray detection is described relative to scintillation crystal 100. One of ordinary skill in the art will recognize, however, that the description given herein with respect to scintillation crystal 100 is equally applicable to gamma ray detection at scintillation crystal 120.

Each photomultiplier tube 110, 135, 140 and 195 is respectively connected to data acquisition unit 150. Data acquisition unit includes hardware configured to process the signals from the photomultiplier tubes. The data acquisition unit 150 measures the arrival time of the gamma ray. The data acquisition unit 150 produces two outputs (one for the combination of PMT 135/140 and one for the combination of PMT 110/195) which encodes the time of the discriminator pulse relative to a system clock (not shown). For a time-of-flight PET system, the data acquisition unit 150 typically produces a time stamp with an accuracy of 15 to 25 ps. The data acquisition unit measures the amplitude of the signal on each PMT (four of the outputs from data acquisition unit 150).

The data acquisition unit outputs are provided to a CPU, 170, for processing. The processing consists of estimating an energy and position from the data acquisition unit outputs and an arrival time from the time stamps output for each event, and may include the application of a many correction steps, based on prior calibrations, to improve the accuracy of the energy, position, and time estimates. As one of ordinary skill in the art would recognize, the CPU 170 can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the electronic memory may be non-volatile, such as ROM, EPROM, EEPROM or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

Alternatively, the CPU 170 may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the CPU 170, the processed signals are stored in electronic storage 180, and/or displayed on display 145. As one of ordinary skill in the art would recognize, electronic storage 180 may be a hard disk drive, CD-ROM drive, DVD drive, FLASH drive, RAM, ROM or any other electronic storage known in the art. Display 145 may be implemented as an LCD display, CRT display, plasma display, OLED, LED or any other display known in the art. As such, the descriptions of the electronic storage 180 and the display 145 provided herein are merely exemplary and in no way limit the scope of the present advancements.

FIG. 10 also includes an interface 175 through which the gamma ray detection system interfaces with other external devices and/or a user. For example, interface 175 may be a USB interface, PCMCIA interface, Ethernet interface or any other interface known in the art. Interface 175 may also be wired or wireless and may include a keyboard and/or mouse or other human interface devices known in the art for interacting with a user.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of imaging a region of interest of an object, the region of interest having an axial extent greater than an axial field of view of a Positron Emission Tomography (PET) scanner, the method comprising:
    determining a minimum number of successive overlapping scans of the PET scanner necessary to image at least the axial extent of the region of interest, wherein each scan of the successive scans has a same axial length equal to the axial field of view of the PET scanner, and each scan overlaps an adjacent scan by a fixed percentage of the axial length of each scan;
    determining a total amount of excess scanning length of the successive scans based on the minimum number of successive scans determined in the determining step, the axial extent of the region of interest, and the axial field of view; and
    determining an initial starting point of a first scan of the successive scans so that the total excess scanning length is equally allocated on each end of the region of interest in an axial direction.

2. The method of claim 1, further comprising:
    scanning the object using the determined number of successive overlapping scans starting from the determined initial starting point.

3. A method of imaging a region of interest of an object, the region of interest having an axial extent greater than an axial field of view of a Positron Emission Tomography (PET) scanner, the method comprising:
    determining a combination of (1) a number of successive overlapping scans of the PET scanner necessary to image the axial extent of the region of interest, wherein each scan of the successive scans has a same axial length equal to the axial field of view of the PET scanner, and (2) an overlap percentage of the axial length of each scan by which each scan overlaps an adjacent scan, so that a total length of the determined number of successive scans exactly equals the axial extent of the region of interest.

4. The method of claim 3, wherein the determining step comprises:
determining the combination of the number of successive overlapping scans and the overlap percentage such that the determined overlap percentage is greater than a predetermined minimum overlap percentage.

5. The method of claim 3, further comprising:
scanning the region of interest using the determined number of successive overlapping scans and the determined scan time.

6. The method of claim 3, further comprising:
setting a scan time for each of the successive scans based on the determined number and the determined overlap percentage.

7. A method of imaging a region of interest in an object, the region of interest having an axial extent greater than an axial field of view of a Positron Emission Tomography (PET) scanner, the method comprising:
determining a minimum number of successive overlapping scans of the PET scanner necessary to image at least the region of interest, wherein each scan of the successive scans has a same axial length equal to the axial field of view of the PET scanner, and each scan overlaps an adjacent scan by a predetermined minimum overlap percentage of the axial length of each scan;
determining a total amount of excess scanning length of the successive scans based on the minimum number of successive scans determined in the determining step, the axial extent of the region of interest, and the axial field of view; and
determining a new overlap percentage based on the determined total amount of excess scanning length and the predetermined minimum overlap percentage, so that a new total amount of excess scanning length, as determined with the new overlap percentage, is zero.

8. The method of claim 7, further comprising:
setting a scan time for each of the successive scans based on an efficiency gain E/L resulting from the new overlap percentage, wherein L is the axial extent of the region of interest and E is the total amount of excess scanning length.

9. The method of claim 7, wherein the step of determining the minimum number of successive overlapping scans comprises:
determining the minimum number n as:

$n = \text{round}\{(L-\alpha_{min}S)/(S-\alpha_{min}S)\}$, wherein L is the axial extent of the region of interest, S is the axial field of view of the PET scanner, $\alpha_{min}$ is the predetermined minimum overlap percentage, and round { } is a function that rounds up to the next integer.

10. The method of claim 9, wherein the step of determining the total amount of excess scanning length comprises:
determining the total amount of excess scanning length E as:

$E = S + (n-1)(1-\alpha_{min})S - L$.

11. The method of claim 10, wherein the step of determining the new overlap percentage comprises:
determining the new overlap percentage α' as:

$\alpha' = \alpha_{min} + E/(n-1)S$.

12. The method of claim 7, further comprising:
scanning the object using the determined number of successive overlapping scans and the determined new overlap percentage.

13. A system for imaging a region of interest in an object, the region of interest having an axial extent greater than an axial field of view of a Positron Emission Tomography (PET) scanner, the system comprising:
the PET scanner configured to scan the object; and
a processor configured to
determine a minimum number of successive overlapping scans of the PET scanner necessary to image at least the axial extent of the region of interest, wherein each scan of the successive scans has a same axial length equal to the axial field of view of the PET scanner, and each scan overlaps an adjacent scan by a predetermined minimum overlap percentage of the axial length of each scan;
determine a total amount of excess scanning length of the successive scans based on the minimum number of successive scans determined in the determining step, the axial extent of the region of interest, and the axial field of view; and
determine a new overlap percentage based on the determined total amount of excess scanning length and the predetermined minimum overlap percentage, so that a new total amount of excess scanning length, as determined with the new overlap percentage, is zero.

14. A non-transitory computer readable medium storing a computer program that, when executed by a computer, causes the computer to perform the steps of:
determining a minimum number of successive overlapping scans of a PET scanner necessary to image at least an axial extent of a region of interest of an object, wherein each scan of the successive scans has a same axial length equal to an axial field of view of the PET scanner, and each scan overlaps an adjacent scan by a predetermined minimum overlap percentage of the axial length of each scan;
determining a total amount of excess scanning length of the successive scans based on the minimum number of successive scans determined in the determining step, the axial extent of the region of interest, and the axial field of view; and
determining a new overlap percentage based on the determined total amount of excess scanning length and the predetermined minimum overlap percentage, so that a new total amount of excess scanning length, as determined with the new overlap percentage, is zero.

* * * * *